United States Patent [19]

Griffis

[11] Patent Number: 4,860,599

[45] Date of Patent: Aug. 29, 1989

[54] APPARATUS FOR SAMPLING HAZARDOUS MATERIALS

[76] Inventor: Steven C. Griffis, 2929 Avenue D, Council Bluffs, Iowa 51501

[21] Appl. No.: 308,821

[22] Filed: Feb. 10, 1989

[51] Int. Cl.$^4$ ............................ G01N 1/04; G01N 1/08
[52] U.S. Cl. .............................. 73/864.45; 73/864.44
[58] Field of Search ........... 73/864.41, 864.43, 864.44, 73/864.45

[56] References Cited

U.S. PATENT DOCUMENTS

| | | | |
|---|---|---|---|
| 3,057,019 | 10/1962 | Hertel | 73/863.41 |
| 3,575,055 | 4/1971 | Thornton | 73/863.43 |
| 3,866,476 | 2/1975 | Thomas | 73/864.25 |

Primary Examiner—Kenneth M. Schor
Assistant Examiner—Gregory R. Muir
Attorney, Agent, or Firm—Zarley, McKee, Thomte, Voorhees & Sease

[57] ABSTRACT

An apparatus for taking bulk samples comprising a housing having sampling tube and a pair of syringes mounted therein. One of the syringes contains a wetting agent which is injected into the material being tested prior to the sampling tube being utilized to remove a sample from the material being tested. The other syringe contains an encapsulating material which is injected into the area from which the sample was taken to seal or encapsulate that area to prevent fiber release into the air after the apparatus has been removed from the material being sampled.

9 Claims, 5 Drawing Sheets

APPARATUS FOR SAMPLING HAZARDOUS MATERIALS

BACKGROUND OF THE INVENTION

This invention relates to an apparatus for taking bulk samples of hazardous materials and more particularly to an apparatus for taking bulk samples from either material which has been wrapped around a pipe or the like or that which is positioned on a wall, floor or ceiling.

Airborne asbestos contamination in buildings is a significant environmental problem. Various diseases have been linked with industrial exposure to airborne asbestos, and the extensive use of asbestos products in buildings has raised concerns about exposure to asbestos in nonindustrial settings. Surveys conducted by the Environmental Protection Agency (EPA) estimate that asbestos-containing materials can be found in approximately 31,000 schools and 733,000 other public and commercial buildings in this country.

In many cases, it is not known whether the material which has been wrapped around pipes or the like is in fact hazardous material such as asbestos or the like. In order to determine whether the material is comprised of asbestos or the like, it is necessary to remove a sample of the material therefrom to analyze the same in a laboratory. However, when the sample is removed from the pipe or the like, fibers are released into the air thereby creating a serious health hazard if it is subsequently found that the material is comprised of asbestos or the like. To the best of applicant's knowledge, a suitable device has not been provided for preventing the release of fibers into the air during the sampling operation or after the sampling operation.

It is therefore a principal object of the invention to provide an apparatus for taking bulk samples of hazardous materials.

A further object of the invention is to provide an apparatus for taking bulk samples of hazardous materials which prevents the release of fibers into the air prior to, during and after the sampling operation.

Yet another object of the invention is to provide an apparatus for taking bulk samples of hazardous materials which may be used to either sample material on pipes, walls, floors, etc.

Still another object of the invention is to provide an apparatus for taking bulk samples of hazardous materials which includes means for positioning the apparatus on a pipe or the like during the sampling operation.

Still another object of the invention is to provide an apparatus for taking bulk samples of hazardous materials which is easy to use.

These and other objects of the invention will be apparent to those skilled in the art.

SUMMARY OF THE INVENTION

An apparatus is described for taking bulk samples of hazardous material without hazardous fibers being released into the air prior to the sampling operation, during the sampling operation or subsequent to the sampling operation. The apparatus comprises a housing having a sampling tube means vertically mounted therein which may be lowered or forced into the material being sampled so that a sample is collected in the sampling tube for subsequent analysis. A pair of syringes are mounted on the apparatus and are provided to enable the injection of a wetting material into the material being tested prior to any sampling operation to reduce the possibility of fibers being released into the air. The other syringe contains an encapsulating material which is injected into the area from which the sample is taken to seal or encapsulate that area to prevent fiber release.

BRIEF DESCRIPTION OF THE DRAWINGS

FIG. 10 is a view similar to FIG. 2 except that a modified version of the apparatus of this invention is illustrated.

DESCRIPTION OF THE PREFERRED EMBODIMENT

Figure 1:
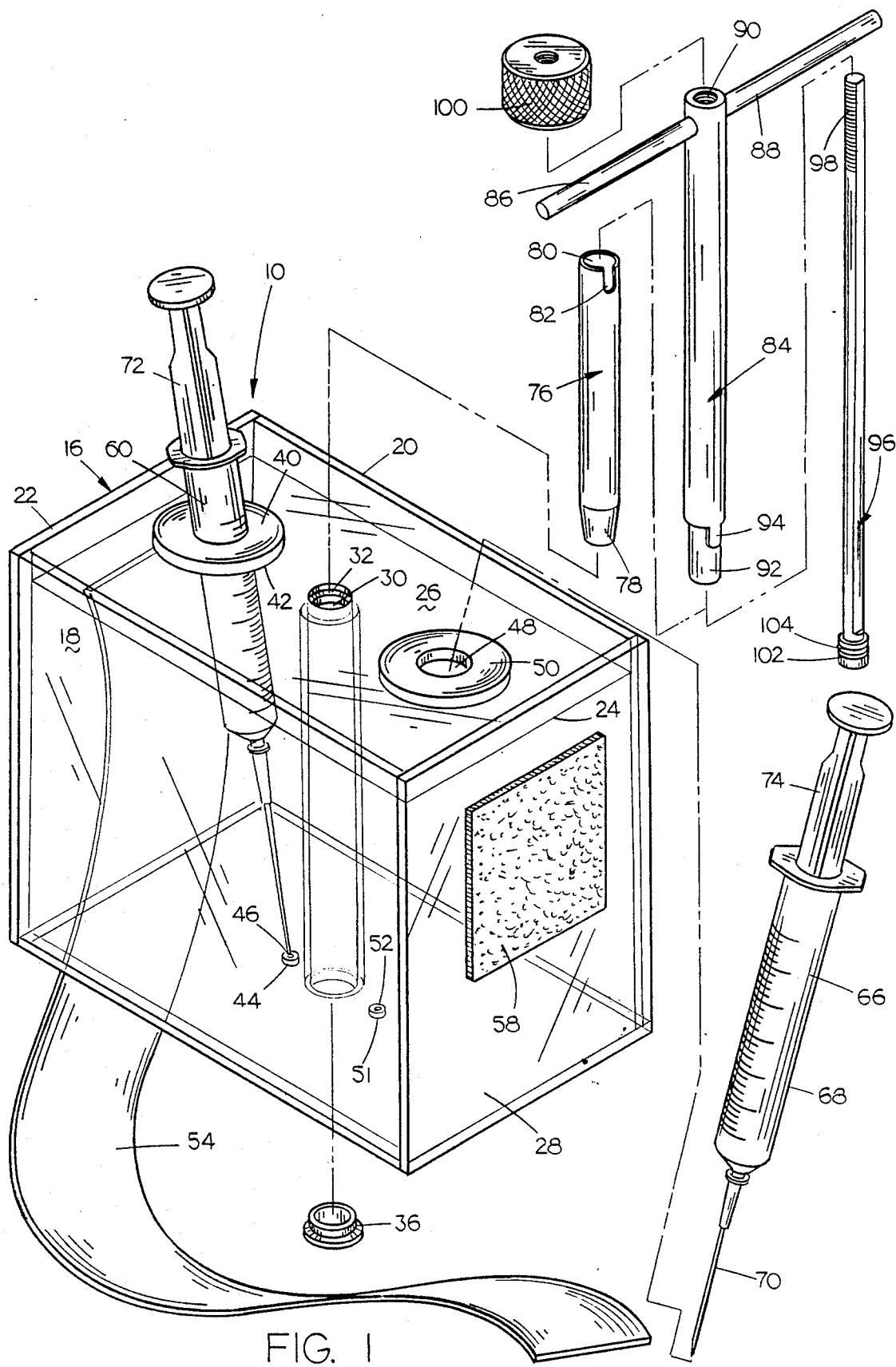
FIG. 1 is an exploded perspective view of the apparatus of this invention.

The preferred apparatus of this invention is illustrated in FIGS. 1-10 and is referred to generally by the reference numeral 10 while the reference numeral 12 refers to a pipe or the like having potentially hazardous material 14 either wrapped thereon or applied thereto. It is the material 14 which is desired to be sampled without releasing hazardous fibers into the air. It can be appreciated that if a sample is simply cut from material 14, the cutting action will release fibers into the air thereby causing potentially dangerous health hazard. Further, even after the sample has been removed from the material 14, that area from which that sample has been removed can also further release hazardous fibers into the air.

Figure 2:
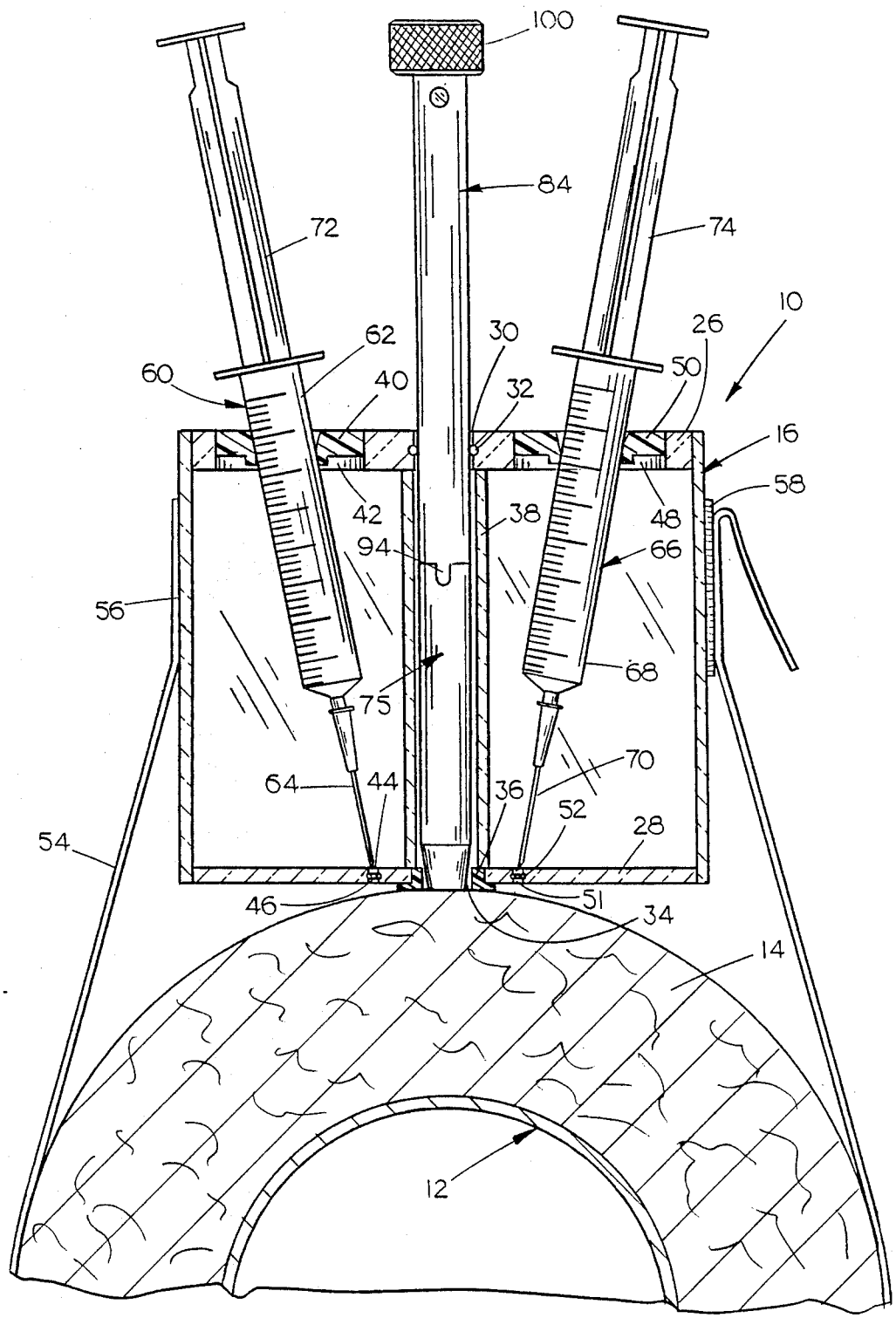
FIG. 2 is a sectional view illustrating the apparatus of this invention mounted on a pipe or the like having the possibly hazardous material thereon.
Figure 3:
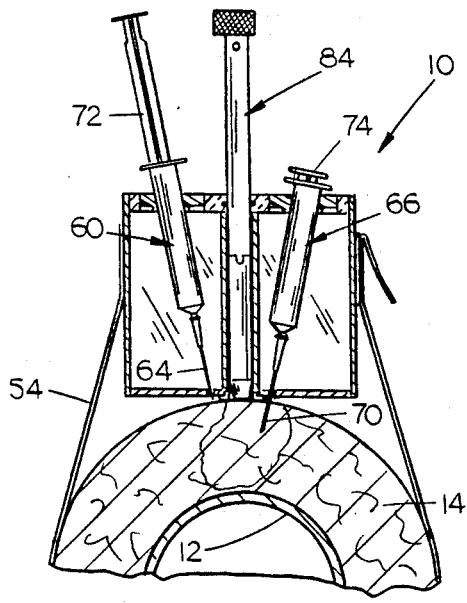
FIG. 3 is a view similar to FIG. 2 except that it illustrates the wetting solution being injected into the hazardous material prior to any sampling.
Figure 4:
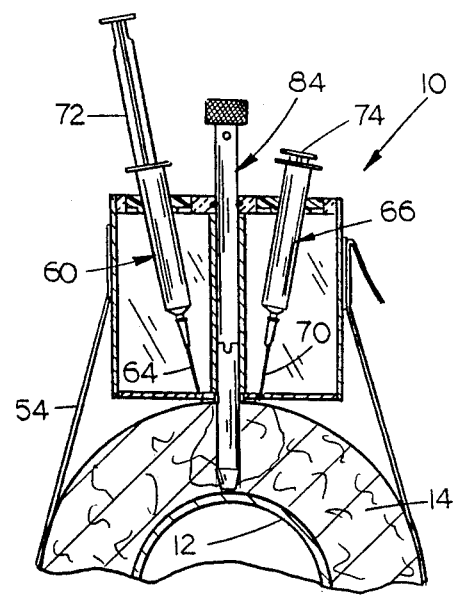
FIG. 4 is a view similar to FIG. 3 except that the wetting solution syringe has been removed from the material and the sampling tube has been inserted into the hazardous material.
Figure 5:
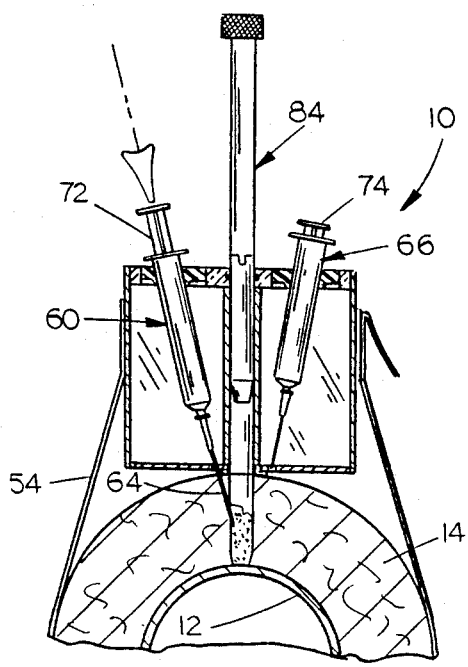
FIG. 5 is a view similar to FIG. 4 except that the sampling tube has been removed from the hazardous material and the encapsulating syringe has been utilized to inject encapsulating liquid into the area from which the sample was taken.

Apparatus 10 generally comprises a transparent housing 16 comprising side walls 18 and 20, end walls 22 and 24, top wall 26 and bottom wall 28. Top wall 26 is provided with an opening 30 (first opening) having an 0-ring 32 mounted therein. Positioned directly below opening 30 is opening 34 (second opening) which has an annular sealing means 36 positioned therein which protrudes below bottom wall 28 as seen in FIG. 2. A transparent tube or cylinder 38 extends between the openings 30 and 34 as seen in FIG. 2.

Top wall 26 is provided with an opening 40 formed therein (third opening) having an annular seal 42 positioned therein. An opening 44 is formed in bottom wall 28 below opening 40 and inwardly therefrom as seen in FIG. 2. Seal 46 is provided in opening 44 as also illustrated in FIG. 2.

Top wall 26 is also provided with an opening 48 which has an annular sealing means 50 positioned therein as best seen in FIGS. 1 and 2. Bottom wall 28 is provided with an opening 51 which is located below and inwardly of opening 48 and which has a seal 52 positioned therein.

One end of a flexible strap 54 is secured to side wall 22 at 56 by any convenient means. The other end of strap 54 will be releasable secured to a Velcro strip 58 in conventional fashion as illustrated in FIG. 2 to enable the apparatus to be mounted on and secured to the pipe 12 as seen in FIG. 2.

The numeral 60 refers to a conventional syringe including a barrel 62 and needle 64 which is adapted to contain a wetting solution or agent such as water.

The numeral 66 refers to a conventional syringe including a barrel 68 and needle 70. Syringes 60 and 66 include movable plungers 72 and 74 respectively.

Figure 7:
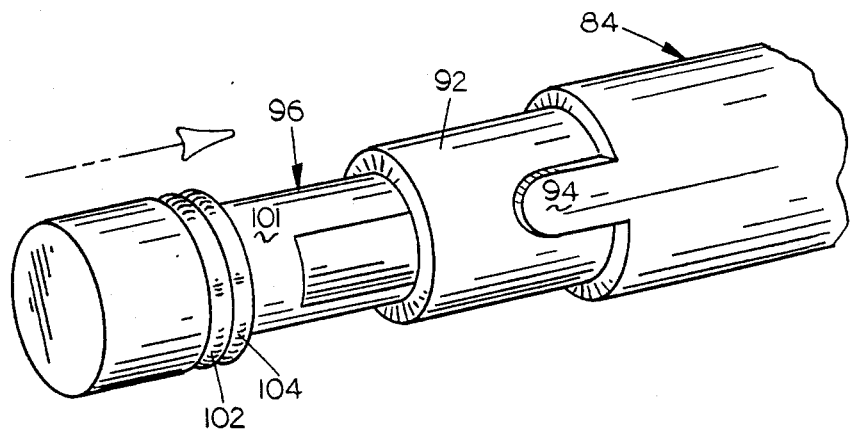
FIG. 7 is a partial perspective view of the end of the handle which is connected to the sampling tube.
Figure 8:
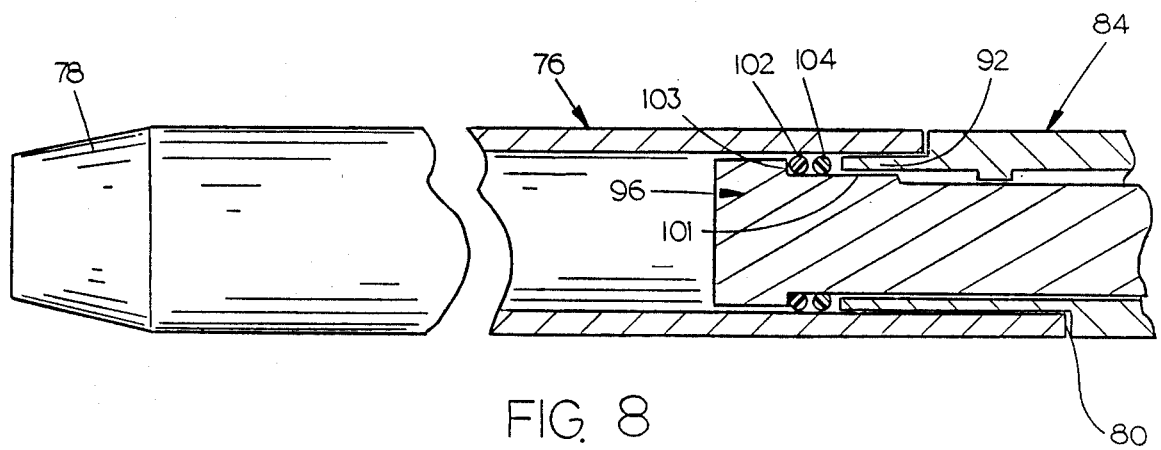
FIG. 8 is a longitudinal sectional view illustrating the sampling tube mounted on the end of the handle prior to being yieldably secured thereto.
Figure 9:
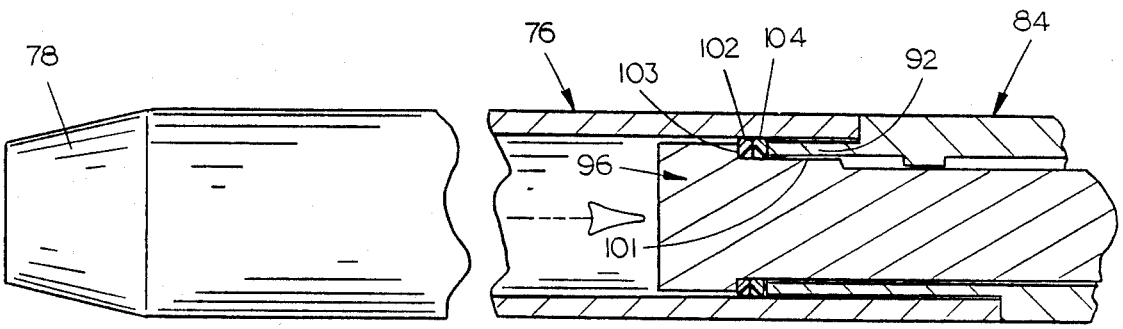
FIG. 9 is a view similar to FIG. 8 except that the handle has been actuated to tighten the connection between the handle and the sampling tube.

The numeral 76 refers to a hollow sampling tube having a sharp tapered lower end 78, open upper end 80 and slot 82 formed therein as seen in FIG. 1. An elongated handle 84 is provided having transversely extending members 86 and 88 at the upper end thereof. Handle 84 is hollow and is provided with open upper end 90, reduced diameter portion 92 at its lower end, and a protrusion 94 which is adapted to be received by the slot 82 as will be described in more detail hereinafter. An elongated actuator 96 extends through handle 84 so that its threaded upper end 98 is positioned above the upper end 90 of handle 84. Nut 100 is threadably mounted on the threaded portion 98 of actuator 96. The lower end of actuator 96 is provided with a reduced diameter portion 101 which defines a shoulder 103 as best seen in FIG. 8. A pair of 0-rings 102 and 104 embrace the reduced diameter portion 101 above shoulder 103 as seen in FIGS. 8 and 9. The handle 84 and the sampling tube 76 cooperate as follows. Actuator 96 is extended upwardly through handle 84 so that the threaded upper end 98 is positioned above the upper end of the handle 84. Nut 100 is partially threaded onto the threaded portion 98 of actuator 96. In this position, the lower end of actuator 96 will be positioned below the lower end of the handle 84 as seen in FIG. 7. Tube 76 is then slipped onto the reduced diameter portion 92 of handle 84 with the protrusion 94 being received in the slot 82. Nut 100 is then threadably rotatably moved relative to actuator 96 so that actuator 96 will be moved upwardly in handle 84 from the position of FIG. 8 to the position of FIG. 9. Upward movement of the actuator 96 causes the 0-ring 104 to move into engagement with the lower end of handle 84 which limits the movement of the 0-rings 102 and 104 but which does not limit the movement of the actuator 96. Continued rotation of the nut 100 causes the 0-rings 102 and 104 to be compressed and expanded outwardly as illustrated in FIG. 9 to frictionally engage the interior surface of the tube 76 to yieldably position or mount the tube 76 on the handle 84. After the sample has been taken and it is desired to remove the tube 76 from the handle 84, knob 100 is threadably rotated to permit actuator 96 to be moved downwardly in the handle 84 thereby repositioning the 0-rings 102 and 104 in the position of FIG. 8 so that tube 76 may be removed from the handle 84. After the sample has been taken, the tube 76 would then normally be inserted into a suitable envelope or the like for transportation to the lab.

In operation, the material 14 on a pipe 12 is to be sampled, the apparatus would normally be positioned on the material 14 through the use of a strap 54 as previously described. Handle 84 and the tube 76 are inserted downwardly through the opening 30 with the seal 32 engaging the outer surface of the tube 76 and the handle 84 during the insertion process. When the apparatus is inserted on the pipe 12 as illustrated, the seal 34 engages the exterior surface of the material 14 as seen in FIG. 2. Syringe 60 will have been previously filled with a wetting agent and the syringe 60 will be positioned as illustrated in FIG. 2. Similarly, syringe 66 will have been previously filled with a suitable encapsulating material and will be positioned as illustrated in FIG. 2.

Figure 6:
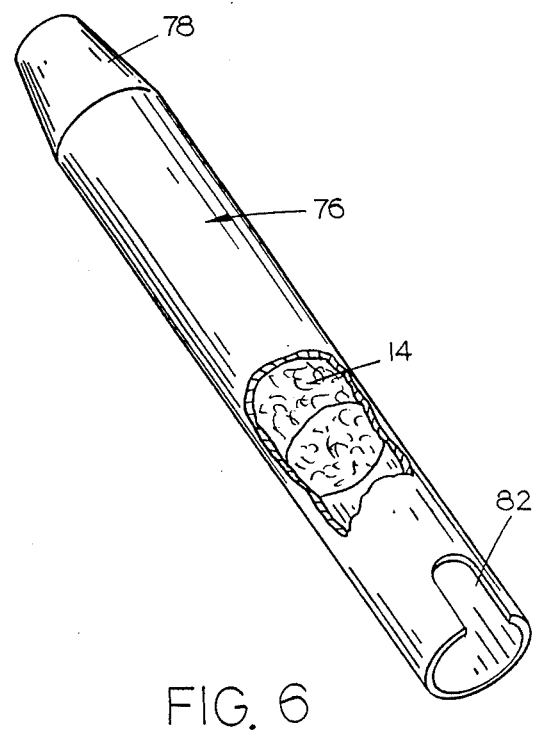
FIG. 6 is a perspective view of the sampling tube with a portion thereof cut away to illustrate the sample therein.

Prior to any sampling operation, syringe 66 is moved downwardly relative to the apparatus so that the needle 70 penetrates the material 14. A suitable amount of the wetting solution or agent is then injected into the material 14 by depressing the plunger 74 which causes the wetting agent to completely wet the material 14 around the area in which the sample is to be taken. When the wetting agent has been injected, the syringe 66 is vertically moved upwardly to the position illustrated in FIG. 4 and the handle 84 is then forced downwardly so that the tapered lower end 78 of the tube 76 penetrates and cuts through the material 14 so that a sample of the material 14 is forced upwardly into the interior of the tube 76 as illustrated in FIG. 6. When the sample has been forced into the interior of the tube 76, the handle 84 is vertically moved upwardly to the position illustrated in FIG. 5. At that time, syringe 60 is vertically moved downwardly so that the needle 64 moves into that area from which the sample has been taken. The encapsulating material in the syringe 60 is then injected into the area from which the sample has been taken to seal or encapsulate that area to prevent any subsequent fiber release into the air. After the encapsulating material has been injected into the material 14 as described, syringe 60 is then vertically moved upwardly so that the needle 64 is withdrawn from the material 14. The entire apparatus may then be removed from the pipe 12. After the apparatus has been removed from the pipe, handle 14 is completely removed from the apparatus and the tube 76 removed therefrom so that the tube 76 and the sample contained therein may be taken to a suitable lab for analysis.

Thus it can be seen that the apparatus of this invention prevents inadvertent release of potentially hazardous fibers into the air prior to the sampling operation, during the sampling operation and subsequent to the sampling operation. The relationship of the various seals with respect to the handle 84, and the syringes 60 and 66 positively prevents any kind of release into the air. Although the apparatus has been described for use on a pipe, it may also be used on a wall or ceiling.

FIG. 10 illustrates a modified version of the apparatus 10 and is referred to by the reference numeral 10'. The only difference in apparatus 10' is that the openings 44 and 51 have been omitted as have the seals 46 and 52. Instead of the needles 64, and 70, passing through seals 46 and 52 respectively, they pass through openings 44' and 51' and enter the material 14 through the opening 34, as seen in FIG. 10.

I claim:

1. A device for taking bulk samples of possible hazardous materials, comprising, a housing means having upper and lower ends and an interior compartment therebetween, a first opening formed in the upper end of said housing means and having a first sealing means extending therearound,, a second opening formed in the lower end of said housing means and having a second sealing means extending therearound, said second opening being positioned directly below said first opening, an elongated cylindrical handle means having upper and lower ends and structured to be extended downwardly through said first opening, an elongated hollow sampling tube selectively removably secured to the lower end of said handle means and having a lower end located such that it will be extended downwardly to penetrate the material being sampled such that the material will be forced into the interior of said sampling tube for subsequent removal, a third opening formed in the upper end of said housing means at one side of said first opening and having an annular sealing means extending therearound for sealably engaging the barrel of a first syringe, a fourth opening formed in the lower end of said housing means at one side of said second opening, a fifth opening formed in the upper end of said housing means at the other side of said first opening and having an annular sealing means extending therearound for sealably engaging the barrel of a second syringe, a sixth opening formed in the lower end of said housing means at the other side of said second opening, a first syringe removably mounted in said housing means such that its barrel is sealably engaged by the annular sealing means in said third opening and such that its needle, may extend through said fourth opening for penetration into the material being sampled so that at least a portion of the contents thereof may be injected into the material around the area where the sample is to be taken by the sampling tube, a second syringe removably mounted in said housing means such that its barrel is sealably engaged by the annular sealing means in said fifth opening and such that its needle may extend through said sixth opening for penetration into the area from which the sample has been taken so that at least a portion of the contents of said second syringe may be injected into said area a wetting solution contained in said first syringe for wetting the area around the sampling location prior to the sample being taken, and an encapsulating solution contained in second syringe for encapsulating the area around the sampling location after the sample has been taken.

2. The apparatus of claim 1 wherein a detachable securing means is mounted on said housing means for selectively mounting, and securing said housing means to a pipe or other conduit having the material to be sampled positioned thereon.

3. The apparatus of claim 2 wherein said securing means comprises an elongated flexible strap means having its ends secured to said housing means.

4. The apparatus of claim 1 wherein said sampling tube has a tapered lower end for penetrating the material being sampled.

5. A device for taking bulk samples of possible hazardous materials, comprising, a housing means having upper and lower ends and an interior compartment therebetween, a first opening formed in the upper end of said housing means and having a first sealing means extending therearound,, a second opening formed in the lower end of said housing means and having a second sealing means extending therearound, said second opening being positioned directly below said first opening, an elongated cylindrical handle means having upper and lower ends and structured to be extended downwardly through said first opening, an elongated hollow sampling tube selectively removably secured to the lower end of said handle means and having a lower end located such that it will be extended downwardly, through said second opening to penetrate the material being sampled such that the material will be forced into the interior of said sampling tube for subsequent removal, a third opening formed in the upper end of said housing means at one side of said first opening and having an annular sealing means extending therearound from sealably engaging the barrel of a first syringe, a fourth opening formed in the upper end of said housing means at the other side of said first opening and having an annular sealing means extending therearound for sealably engaging the barrel of a second syringe, a first syringe removably mounted in said housing means such that its barrel is sealably engaged by the annular sealing means in said third opening and such that is needle may extend through said second opening for penetration into the material being sampled so that at least a portion of the contents thereof may be injected into the material around the area where the sample is to be taken by the sampling tube, a second syringe removably mounted in said housing means such that its barrel is sealably engaged by the annular sealing means in said forth opening and such that its needle may extend through said second opening for penetration into the area from which the sample has been taken so that at least a portion of the contents of said second syringe may be injected into said area, a wetting solution contained in said first syringe for wetting the area around the sampling location prior to the sample being taken, and an encapsulating solution contained in said second syringe for encapsulating the area around the sampling location after the sample has been taken.

6. The apparatus of claim 5 wherein a detachable securing means is mounted on said housing means for selectively mounting and securing said housing means to a pipe or other conduit having the material to be sampled positioned thereon.

7. The apparatus of claim 6 wherein said securing means comprises an elongated flexible strap means having its ends secured to said housing means.

8. The apparatus of claim 5 wherein said sampling tube has a tapered lower end for penetrating the material being sampled.

9. The apparatus of claim 5 wherein a cylindrical tube means extends between said first and second openings and is structured so as to receive said cylindrical handle and sampling tube, said cylindrical tube means having a pair of openings formed therein adjacent its lower end for receiving the needles of said first and second syringes respectively at times.

* * * * *